US005703130A

United States Patent [19]
Han et al.

[11] Patent Number: 5,703,130
[45] Date of Patent: Dec. 30, 1997

[54] CHALCONE RETINOIDS AND METHODS OF USE OF SAME

[75] Inventors: Rui Han; Zong-Ru Guo, both of Beijing, China

[73] Assignee: Institute of Materia Medica, an Institute of the Chinese Academy of Medical Sciences, Beijing, China

[21] Appl. No.: 657,886

[22] Filed: Jun. 7, 1996

[51] Int. Cl.$^6$ .......................... A61K 31/16; C07C 233/65
[52] U.S. Cl. .......................... 514/616; 514/533; 514/534; 514/535; 514/621; 514/563; 560/43; 560/53; 560/61; 560/74; 562/452; 562/455; 564/158; 564/169
[58] Field of Search .......................... 514/533, 534, 514/535, 621, 563; 560/43, 53, 61, 74; 562/452, 455; 564/158, 169

[56] References Cited

U.S. PATENT DOCUMENTS

| | | |
|---|---|---|
| 3,541,097 | 11/1970 | Beyerle et al. . |
| 3,880,910 | 4/1975 | Spivac et al. .......................... 260/473 S |
| 3,979,360 | 9/1976 | Spivac et al. .................... 260/48.85 B |
| 4,124,693 | 11/1978 | Gander et al. . |
| 4,144,336 | 3/1979 | Boltze et al. . |
| 4,151,179 | 4/1979 | Appleton et al. . |
| 4,190,594 | 2/1980 | Gander et al. . |
| 4,310,546 | 1/1982 | Gander . |
| 4,323,581 | 4/1982 | Gander . |
| 4,385,175 | 5/1983 | Just et al. . |
| 4,523,042 | 6/1985 | Loev et al. . |
| 4,602,034 | 7/1986 | Briet et al. . |
| 4,713,465 | 12/1987 | Kramer et al. . |
| 4,783,533 | 11/1988 | Briet et al. . |
| 4,960,908 | 10/1990 | Ito et al. . |
| 5,096,713 | 3/1992 | Philippe et al. . |
| 5,096,924 | 3/1992 | Ishizuka et al. . |
| 5,116,954 | 5/1992 | Briet et al. . |
| 5,124,083 | 6/1992 | Shealy . |
| 5,141,746 | 8/1992 | Fleury et al. . |

FOREIGN PATENT DOCUMENTS

| | | |
|---|---|---|
| 1127170 | 7/1982 | Canada . |
| 0404039 | 6/1990 | European Pat. Off. . |
| 2364122 | 6/1974 | Germany . |
| 2420705 | 9/1974 | Germany . |
| 6-116143 | 4/1994 | Japan . |
| 6-247919 | 9/1994 | Japan . |
| 950714 | 2/1964 | United Kingdom . |
| 9323357 | 11/1993 | WIPO . |

OTHER PUBLICATIONS

Blazsek et al., *Retinoic acid in mono–or combined differentiation therapy of myelodysplasia and acute promyelocytic leukemia*, Biomed & Pharmacother, vol. 45, pp. 169–177, 1991.

Abstract— Cassidy et al., *Recent Advances in the Discovery of Potential Cancer Chemopreventive Agents*, Abstract Collection of International Symposium on Recent Advances in Chemistry and Molecular Biology of Cancer Research, Beijing, China, pp. 5–6, 1991.

Castaigne et al., *All–Trans Retinoic Acid as a Differentiation Therapy for Acute Promyelocytic Leukemia. I. Clinical Results*, Blood, vol. 76, No. 9, pp. 1704–1709, 1 Nov. 1990.

Chomienne et al., *All–Trans Retinoic Acid in Acute Promyelocytic Leukemias. II. In Vitro Studies: Structure–Function Relationship*, Blood, vol. 76, No. 9, pp. 1710–1717, 1 Nov. 1990.

Chomienne et al., *Structure–Activity Relationships of Aromatic Retinoids on the Differentiation of the Human Histiocytic Lymphoma Cell Line U–937*, Leukemia Research, vol. 10, No. 11, pp. 1301–1305, 1986.

Clarkson, *Retinoic Acid in Acute Promyelocytic Leukemia: The Promise and the Paradox*, Cancer Cells, vol. 3, No. 6, pp. 211–220, Jun. 1991.

Dawson et al., *Aromatic Retinoic Acid Analogues. Synthesis and Pharmacological Activity*, Journal of Medicinal Chemistry, vol. 24, No. 5, pp. 583–592, 1981.

Dawson et al., *Conformationally Restricted Retinoids*, J. Med. Chem., vol. 27, No. 11, pp. 1516–1531, 1984.

Degos, *All–trans retinoic acid (ATRA) therapeutical effect in acute promyelocytic leukemia*, Biomed & Pharmacother, vol. 46, pp. 201–209, 1992.

Abstract— Du et al., *Comparison of Toxicities of 4–(ethoxycarbophenyl) Retinamide and Some Other Retinoids*, Institute of Materia Medica, vol. 18, No. 5, 1982.

Edwards et al., *Chalcones: A New Class of Antimitotic Agents*, J. Med. Chem., vol. 33, pp. 1848–1954, 1990.

Egan et al., *The Pharmacology, Metabolism Analysis, and Applications of Coumarin and Coumarin–Related Compounds*, Drug Metabolism, Reviews, vol. 22, No. 5, pp. 503–529, 1990.

Abstract— Han et al., *Effects of S86019, An Active Component From Puralia Lobata, On Cell Differentiation and Cell Cycle Traverse of HL–60 Cells*, Chinese Journal of Cancer Research, vol. 2, No. 3, pp. 51–53, 1990.

Han et al., *Evaluation of N–4–(Hydroxycarbophenyl) Retinamide as a Cancer Prevention Agent and as a Cancer Chemotherapeutic Agent*, In Vivo, vol. 4, pp. 153–160, 1990.

Harvey et al., *A New Coumarin Synthesis and Its Utilization for the Synthesis of Polycyclic Compounds with Anticarcinogenic Properties*, J. Org. Chem., vol. 53, No. 17, pp. 3936–3943, 1988.

Harvey et al., *A New Chromone and Flavone Synthesis and Its Utilization for the Synthesis of Potentially Antitumorigenic Polycyclic Chromones and Flavones*, J. Org. Chem., vol. 55, No. 25, pp. 6161–6166, 1990.

(List continued on next page.)

*Primary Examiner*—Shailendra Kumar
*Attorney, Agent, or Firm*—Browdy and Neimark

[57] ABSTRACT

New retinoid compounds, as chalcone retinoids and compositions thereof, are provided which exhibit therapeutic and/or biological activity on cancer or precancer cells, as well as to methods of use of same.

5 Claims, No Drawings

OTHER PUBLICATIONS

Abstract— Ito et al., *Synthesis and Structure–Activity Relationship of Potential Inhibitors of Benzo[a]–pyrene Carcinogenesis*, Abstract Collection of International Symposium on Recent Advances in Chemistry and Molecular Biology of Cancer Research, Beijing, China, pp. 68–69, 1991.

Abstract— Jing et al., *Differentiation of B16 Melanoma Cells Induced by Daidzein*, Chinese Journal of Pharmacology And Toxicology, vol. 6, No. 4, pp. 278–280, Nov. 1992.

Kizaki et al., *Differentiation–Inducing Agents in the Treatment of Myelodysplastic Syndromes*, Seminars in Oncology, vol. 19, No. 1, pp. 95–105, Feb. 1992.

Kagechika et al., *Retinobenzoic Acids. 3. Structure–Activity Relationships of Retinoidal Azobenzene–4–carboxylic Acids and Stilbene–4 carboxylic Acids*, J. Med. Chem., vol. 32, pp. 1098–1108, 1989.

LoCoco et al., *Molecular Evaluation of Response to All––Trans–Retinoic Acid Therapy in Patients With Acute Promyelocytic Leukemia*, Blood, vol. 77, No. 8, pp. 1657–1659, 15 Apr. 1991.

Middleton, Jr., *Effects of Flavonoids on Immune and Inflammatory Cell Functions*, Biochemical Pharmacology, vol. 43, No. 6, pp. 1167–1179, 1992.

Nair et al., *Novel Coumarins as Potential Anticarcinogenic Agents*, Carcinogenesis, vol. 12, No. 1, pp. 65–69, 1991.

Newton et al., *Structure–Activity Relationships of Retinoids in Hamster Tracheal Organ Culture*, Cancer Research, vol. 40, pp. 3413–3425, Oct. 1980.

Preuss–Ueberschar et al., Drug Res., vol. 34, pp. 1305–1313, 1984.

Sato et al., *Functional Studies of Newly Synthesized Benzoic Acid Derivatives: Identification of Highly Potent Retinoid––Like Activity*, Journal of Cellular Physiology, vol. 135, pp. 179–188, 1988.

Shealy et al., *Terminal Bifunctional Retinoids. Synthesis and Evaluation Related to Cancer Chemopreventive Activity*, J. Med. Chem., vol. 31, pp. 1124–1130, 1988.

Skrede et al., *Retinyl Esters in Chylomicron Remnants Inhibit Growth of Myeloid and Lymphoid Leukaemic Cells*, European Journal of Clinical Investigation, vol. 21, pp. 574–579, 1991.

Smith et al., *Retinoids in Cancer Therapy*, Journal of Clinical Oncology, vol. 10, vo. 5, pp. 839–864, May 1992.

Abstract— Song et al., *Differentiation of Human Promyelocytic Leukemia (HL–60) Cells Induced By New Synthetic Retinoids 4–(Ethoxycarbophenyl) Retinamide and 4–(hydroxycarbophenyl) Retinamide*, Institute of Materia Medica, Chinese Academy of Medical Sciences, pp. 576–581, 1984.

Warrell, Jr., *All–Trans–Retinoic Acid: What Is It Good For?* Journal of Clinical Oncology, vol. 10, No. 11, pp. 1659–1661, Nov. 1992.

S. Shibata, *Anti–tumorgenic chalcones*, Stem Cells, vol. 12:44–62, 1994.

Srivastava et al. *Effect of quercetin on serine/threonine and tyrosine protein kinase*, Plant Flavonoids in Biology and Medicine: Biochemical, Pharmacological and Structure–Activity Relationships, pp. 315–318, 1986.

Piantelli et al. *Type II Estrogen Binding Sites and Antiproliferative Activity of Quercetin in Human Meningiomas*, Cancer, vol. 71:193–199, 1993.

B. Havsteen, *Flavonoids, A Class of Natural Products of High Pharmacological Potency*, Biochemical Pharmacology, vol. 32:1141–1148.

Chae et al. *Effects of synthetic and naturally occurring flavoniods on benzo[a]pyrene metabolism by hepatic microsomes prepared from rats treated with cytochrome P–450 inducers*, Cancer Letters, vol. 60, pp. 15–24, 1991.

M.E. Marshall et al. *Growth–inhbitory effects of coumarin (1,2–benzopyrone) and 7–hydroxycoumarin on human manlignant cell lines in vitro*, J. Cancer Res. & Clin. Oncol., vol. 120, pp. s3–s10, 1994.

Bibby et al. *Flavone acetic acid–from Laboratory to clinic and back*, Anti–Cancer Drugs, vol. 4, pp. 3–17, 1993.

Jing et al. *Structural Requirements for Differentiation–Induction and Growth–Inhibition of Mouse Erythroleukemia Cells by Isoflavones*, Anticancer Research, vol. 15, pp. 1147–1152, 1995.

Middleton et al. *Effects of Flavonoids on Immune and Inflammatory Cell Functions*, Biochemial Pharmacology, vol. 43, No. 6, pp. 1167–1179, 1992.

Chemical Abstracts, vol. 122, No. 13, 27 Mar. 1995, Columbus, Ohio, US; abstract No. 151372M, Kaku S.: "Benzoates and IgE formation inhbitors containing them", p. 151380.

CHALCONE RETINOIDS AND METHODS OF USE OF SAME

CROSS-REFERENCE TO RELATED APPLICATION

This application claims the benefit of U.S. Provisional Application No. 60/000,057, filed Jun. 8, 1995.

BACKGROUND OF THE INVENTION

1. Field of the Invention

The present invention relates to novel retinoids, as coumarin retinoids and/or purine retinoids, and compositions thereof, which exhibit therapeutic and/or biological activity on cancer or precancer cells, as well as to methods of using same.

2. Description of the Related Background Art

Retinoids play an important role in the development and differentiation of epidermal cells, as well as in reversing precancerous lesions. Clinical trials have been conducted using N-(4-carboxyphenyl) retinamide in the treatment of some precancerous lesions, oral leukoplakia, vulval leukoplakia, atypical dysplasia of the cervix and the gastric mucosa, and the like (Hah et al., in vivo 4:153–160 (1990)). Other retinoids, such as isoretinoin and etretinate, are in current use as prescription drugs for the treatment of acne and psoriasis (Gander et al., U.S. Pat. No. 4,126,693).

However, retinoids have a significant level of toxicity, and treatment using known retinoid agents suffers from problems due to the level of toxicity and side effects which accompany administration of known retinoid compounds. Accordingly, there exists a need to provide novel compounds having retinoid activity but which have less toxicity and/or side effects.

Smith et al., *J. Clin. Oncol.* 10 (5):839–864 (1992), reviews the use of retinoids in cancer therapy with most of the emphasis on anti-tumor effects in patients with acute promyelocytic leukemia (APL). Smith et al. reports that the natural retinoid, all-trans-retinoic acid (RA),

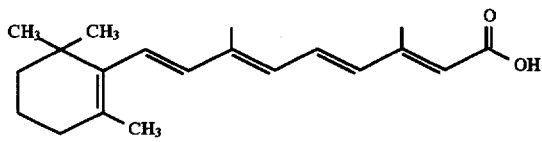

induces cell differentiation in some human acute myeloid leukemia (AML), neuroblastoma, teratocarcinoma, melanoma, and rat rhabdomyosarcoma cells and also appears to play an essential role in the normal differentiation of epithelial cells. Clinical toxicities associated with the use of RA in dermatologic studies are listed in Table 6 of the Smith et al. reference with disclosure in the text that retinoids are recognized as powerful teratogens.

Kizaki et al., *Seminars in Oncology* 19 (1):95–105 (1992), reports that retinoids are potent anti-carcinogenic agents in many experimental models and that they inhibit growth and induce differentiation of transformed neoplastic cells. A number of references specifically relate to retinoic acid derivatives as anti-cancer agents. Just et al., U.S. azetidinones useful as anti-cancer agents. Philippe et al., U.S. Pat. No. 5,096,713, discloses retinoic esters of L-cladinose which exhibit anti-tumor activity. The Paust Canadian Patent No. 1,127,170, is specifically directed to retinic acid N-(carboxy)-phenylamindes and 7,8-dehydro-retinic acid N-(carboxy)-phenylamides, and discloses that, while the retinic compounds are predominantly directed toward preventing cancer, they may be used for therapeutic treatment of tumors of the bladder, the mammary gland, the skin and the mucous membranes.

A number of references disclose retinoids being used in cancer prophylaxis and as inducers of cell differentiation. For instance, Newton et al., *Cancer Res.* 40:3413–3425 (1980) discloses a long list of esters, amines and amides of retinoic acid and their activity in cancer prophylaxis. None of the listed compounds are related to flavonoids or chalcone retinoids. Du et al., *Inst. Mater. Med. Chinese Acad. Med. Sci. Beijing* 17:331–337 (1982), discloses the retinamides $R_{II}$ (N-4(hydroxycarbophenyl) retinamide) and $R_I$ (4-(ethoxycarbylphenyl)-retinamide) and their utility as cancer preventatives. Song et al., *Inst. Mater. Med. Chinese Acad. Med. Sci. Beijing* 19:576–581 (1984), also relates to the property of the retinamides $R_I$ and $R_{II}$ as cell differentiation inducers. The Shealy patent, U.S. Pat. No. 5,124,083, discloses derivatives of retinoic acid as cell differentiation agents for cancer prevention and treatment and the Shealy et al. publication, *J. Med. Chem.* 31:1124–1130 (1988), discloses the chemopreventative activity of bifunctional retinoic acid esters. Dawson, *J. Med. Chem.* 27:1516–1531 (1984), Dawson et al., *J. Med. Chem.* 24:583–592 (1981), Kagechika et al., *J. Med. Chem.* 32:1098–1108 (1989), Skrede et al., *Eur. J. Clin. Investig.* 21:574–579 (1991) and Loev et al., U.S. Pat. No. 4,523,042, all disclose various retinoid compounds which are cell differentiation agents. Gander, U.S. Pat. No. 4,323,581, discloses the use of N-(4-hydroxyphenyl)-all-trans-retinamide for treatment of breast cancer while in U.S. Pat. No. 4,310,546, Gander discloses the use of N-(4-acyloxyphenyl)-all-trans-retinamide in the prevention of epithelial cancer. The Gander et al. patents, U.S. Pat. Nos. 4,126,693 and 4,190,594, relate to other properties of esters and amides of retinoic acids.

Furthermore, Blazsek et al., *Biomed. Pharmacother.* 45:169–177 (1991), Degos, *Biomed. Pharmacother.* 46:201–209 (1992), Castaigne et al., *Blood* 76 (9):1704–1709 (1990), Chomienne et al., *Blood* 76 (9):1710–1717 (1990), and Lo Coco et al., *Blood* 77 (8):1657–1659 (1991) all disclose using retinoic acid in differentiation therapy for patients with acute promyelocytic leukemia (APL).

Some flavonoids and chalcones have been found to have anti-tumor properties. Middleton et al., *Biochem. Pharmacol.* 43:1167–1179 (1992), relates to the anti-tumor effects of flavonoids, and Harvey et al., *J. Org. Chem.* 53:3936–3943 (1988) and *J. Org. Chem.* 55:6161–6166(1990), and Nair et al., *Carcinogenesis* 12(1):65–69(1991) relate to anti-carcinogenic coumarin and flavone compounds. Jing et al., *Chinese J. Pharmacol. Toxicol.* 6 (4):278–280 (1992) discloses that an isoflavone, diadzein, inhibits melanoma cell growth. The Ishizuka et al. patent, U.S. Pat. No. 5,096,924, discloses anti-cancer effects of a substituted 2-benzopyrinone. Ito et al., U.S. Pat. No. 4,960,908, Briet et al., U.S. Pat. Nos. 4,602,034, 4,783,533, and 5,116,954, and Kramer et al., U.S. Pat. No. 4,713,465, all teach 4-benzopyrinone compounds as anti-cancer agents.

Preuss-Ueberschar et al., *Drug Res.* 34:1305–1313 (1984) discloses that benzopyrones, which include coumarin, are not teratogenic. The pharmacology of coumarin-related compounds is reviewed by Egan et al. which indicates that coumarin-related compounds are known to inhibit the carcinogenicity of carcinogens and that coumarin has been tested for treatment of melanoma.

Edwards et al., *J. Med. Chem.* 33:1948–1954 (1990) relates to the anti-mitotic action of chalcones. Cassady et al. and ito et al., *Abstract Collection of International Sympo-*

*sium on Recent Advance in Chemistry and Molecular Biology of Cancer Research*, Beijing, China, 1991, pp. 5-6 and 68-69, respectively, relate to the anti-mitogenic effects of various flavonoids, including biochanin A.

Han et al., *Chinese J. Cancer Res.* 2 (3):51-53 (1990), reports the effects of an isoflavone, S86019, which is an active component of a medicinal herb used in China, *Pueraria lobata*. The structure of S86019 is not disclosed. In a different publication, in vivo 4:153-160 (1990), Han et al. evaluates the $R_{II}$ retinamide compound as a cancer prevention agent and as a cancer chemotherapeutic agent and discusses the induction of cell differentiation of HL60 cells using a combination treatment of $R_{II}$ with S86019. The combination of $R_{II}$ with S86019 acts synergistically in inducing cell differentiation and it is reported that this combination may have clinical applications with minimal patient toxicity.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to overcome one or more deficiencies of the related art, in particular, to overcome the teratogenicity associated with retinoids.

Another object of the present invention is to provide novel retinoids, as chalcone retinoids, which have anti-neoplastic activity in vitro.

A further object of the present invention is to provide novel retinoids, as chalcone retinoids, which have anti-neoplastic activity in vivo.

A still further object of the present invention is to provide novel retinoid compounds and compositions, using methods of the present invention, which compounds and/or compositions are useful for research and/or pharmaceutical applications in mammals, particularly humans.

The presently claimed retinoid compounds and compositions synergistically combine the cell differentiation activity of retinoids with the mitotic inhibitor activity of chalcones.

One utility of the present invention is the use of such retinoids as a comparative compound or composition for in vitro testing of other compounds for anti-neoplastic activity. Such retinoids are also useful as chemotherapeutic agents in vitro, in situ and/or in vivo.

Yet another object of the present invention is to provide synthetic methods for obtaining retinoid compounds and/or compositions according to formula (I) as descriptively enabled herein.

Furthermore, the invention is also directed to a method for treating a subject having a precancer or a cancer-related pathology by administering at least one retinoid compound and/or composition comprising or consisting essentially of a chalcone retinoid, optionally further comprising or consisting essentially of at least one anti-cancer pharmaceutical and/or immunomodulator.

Other features, advantages, embodiments, aspects and objects of the present invention will be clear to those skilled in the areas of relevant art, based on the description, teaching and guidance presented herein.

DETAILED DESCRIPTION OF PREFERRED EMBODIMENTS

The present invention provides a new and biologically active group of retinoids which display cancer chemoprevention activity. These derivatives include, but are not limited to, compounds according to the following formula (I) as chalcone retinoids.

The chalcone retinoids in accordance with the present invention have the following formula (I):

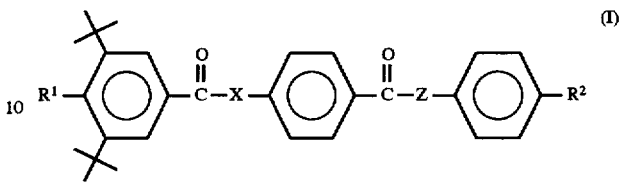

(I)

wherein $R^1$=OH or $C_1$–$C_5$ alkoxy; $R^2$=OH, carboxy, $C_1$–$C_6$ alkyl ester, or NHCOR$^3$ where $R^3$ is methyl, ethyl, propyl or butyl; X=NH or $C_2$–$C_4$ alkenyl; and Z=NH or O. $R^2$ is preferably selected from the group consisting of OH, $COOC_2H_5$, $COOC_3H_7$, $COOCH_3$, COOH, $NHCOCH_3$, $NHCOCH_2CH_3$. X as an alkenyl is preferably CH=CH.

The following compounds (I-A)–(I-S) shown in Table 1 are non-limiting examples of compounds according to formula (I), and such compounds in any combination are provided as compounds or compositions according to the present invention:

TABLE 1

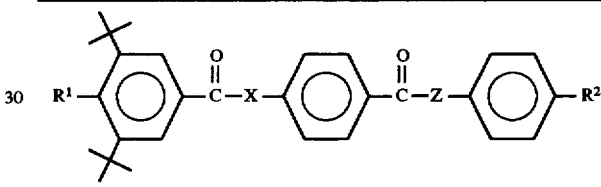

| Compound | R$^1$ | R$^2$ | X | Z |
|---|---|---|---|---|
| (I-A) | OH | OH | NH | NH |
| (I-B) | OH | NHCOCH$_3$ | NH | O |
| (I-C) | OH | COOC$_2$H$_5$ | NH | NH |
| (I-D) | OH | COOH | NH | NH |
| (I-E) | OH | OH | CH=CH | NH |
| (I-F) | OH | NHCOCH$_3$ | CH=CH | O |
| (I-G) | OH | COOC$_2$H$_5$ | CH=CH | NH |
| (I-H) | OH | COOH | CH=CH | NH |
| (I-I) | CH$_3$O | OH | NH | NH |
| (I-J) | CH$_3$O | NHCOCH$_3$ | NH | O |
| (I-K) | CH$_3$O | COOC$_2$H$_5$ | NH | NH |
| (I-L) | CH$_3$O | COOH | NH | NH |
| (I-M) | CH$_3$O | OH | CH=CH | NH |
| (I-N) | CH$_3$O | NHCOCH$_3$ | CH=CH | O |
| (I-O) | CH$_3$O | COOC$_2$H$_5$ | CH=CH | NH |
| (I-P) | CH$_3$O | COOH | CH=CH | NH |
| (I-Q) | OH | NHCOH$_3$ | O | O |
| (I-R) | OH | COOC$_2$H$_5$ | O | NH |
| (I-S) | OH | COOH | O | NH |

Such compounds, or isomers thereof, in any combination are provided as compounds or compositions according to the present invention.

Such retinoids of the present invention are unexpectedly discovered to have anti-cancer activity, thus providing suitable compounds and compositions for treatment of cancer-related pathologies, optionally with additional pharmaceutically active ingredients, such as antiviral, chemotherapeutic agents and/or immuno-stimulating compounds, or antiviral antibodies or fragments thereof, in vitro, in situ, and/or in vivo.

Cancer-related pathologies in the context of the present invention include, but are not limited to, tumors and pathologies involving tumorigenesis, leukemias, lymphomas, melanomas, sarcomas, virus-related cancers, and any other known cancers.

The term "anti-cancer activity" is intended to mean the ability to induce at least one of (1) inhibition of growth or mitosis of transformed, mutated, preneoplastic or neoplastic cells; (2) promotion of apoptosis; and/or (3) angiogenesis inhibition.

In the context of the present invention, the term inhibition or stimulation, as a quantitative value, is between 10 and 100 percent inhibition and 10 and 1000 percent stimulation, relative to a suitable control, such as, but not limited to the same cell or animal under the same conditions, except for the presence or administration of one or more retinoids according to the present invention.

The present invention also provides synthetic methods for obtaining retinoid compounds according to formula (I), which would be clear to one of ordinary skill in the art, based on the teaching and guidance presented herein, in combination with what is known in the related fields of art. In general, components of completely synthesized chalcone compounds and/or retinoyl compounds can be provided as starting materials, and the appropriate side groups can be added, modified or used in suitable, known chemical reaction steps to provide retinoid compounds according to formula (I).

In one non-limiting method for making retinoid compounds according to formula (I), a solution of a specific molar amount (e.g., 2.5 mmole) of a chalcone derivative is provided in a suitable amount (e.g., 20 ml) of an anhydrous organic solvent (e.g., anhydrous tetrahydrofuran (THF)), and a slight excess (e.g., 2.75 mmole) of a secondary or tertiary alkyl substituted amine (e.g., triethylamine) is added. To this mixture, with stirring, an excess molar amount (e.g., 2.75 mmole) of an alkyl halo formate (e.g., ethyl chloroformate) is added dropwise and stirred at room temperature for 0.2–3.0 hours (e.g., 1 hr.). Petroleum ether is then added and the separated solid filtered. The filtrate is then concentrated in vacuo to dryness. A suitable amount of anhydrous organic solvent (e.g., 20 ml of anhydrous acetonitrile) is added to the filtrate and an equal molar amount of an alkyl substituted phenol (e.g., 2.5 mmole of acetaminophenol) is then added.

The mixture is then warmed to a clear solution and a suitable amount (e.g., 0.25 g) of the secondary or tertiary alkyl substituted amine (e.g., triethylamine) and another suitable amount (e.g., 20 mg) of a disubstituted alkyl amino pyridine (e.g., 4-dimethylaminopyridine) is added while stirring. The mixture is heated to 40°–60° C. (e.g., 50° C.) for 0.5–3 hours (e.g., 1 hr.) to concentrate the mixture to half its original volume by solvent removal. Crystals formed from the concentration of the mixture are collected, washed, and recrystallized from 90–99% alcohol (e.g., 95% ethanol), to obtain 60–99% of the purified retinoid compound of the present invention.

Testing Anti-Cancer Activity

There are many known in vitro assays for determining whether a given compound and/or composition has anti-neoplastic activity. Such methods are well known in the art and provide the means for one of ordinary skill in the art to determine, using routine experimentation, whether a given retinoid of the present invention has a specific anti-cancer activity for a given cancer-related pathology.

The following are examples of methods which can be used to screen chalcone retinoids according to formula (I) for determining at least one pharmaceutical utility; without undue experimentation, based on the teaching and guidance presented herein.

Non-limiting examples of anti-neoplastic in vitro activity, include but are not limited to, activity (1) against phosphorylation of phospholipids promoted by tetradecanoylphorbol-13-acetate in HeLa cells as a screening test for anti-tumor promoting effect; (see, e.g., Shibata, *Stem Cells* 12:44–52 (1994)); (2) soft agar clonogenic assays (e.g., Rangel et al., *Cancer Chemother. Pharmacol.* 33:460–64 (1994)); (3) cytostatic activity in cancer cells (see, e.g., Rajala et al., *Ann. Chir. Gynacol. Suppl.* 206:50–53 (1993)); inhibition of proliferation of human gastric cancer derived cells (Shibata, supra); (3) cytotoxic activity against cancer cell systems (see, e.g., Ngassapa et al., *J. Nat. Prod.* 56:1676–81 (1993); Sanyal et al., *Neoplasma* 40:219–22 (1993); Perez et al., *Cancer Chemother. Pharmacol.* 33:245–250 (1993)); Hahn et al., *Cancer* 72:2705–11 (1993)); (4) inhibition of tumor colony forming units (see, e.g., Eckardt et al., *J. Nat'l Cancer Inst.* 86:30–33 (1994); Chen et al., *Anticancer Drugs* 4:447–57 (1993)); (5) cell differentiation of human promyelocytic leukemia cells; and (6) MTT assay for inhibition of cancer cells, the contents of which references are entirely incorporated herein by reference.

Non-limiting examples of anti-neoplastic in vivo activity include, but are not limited to, activity in (1) inhibition of tumorigenesis in mouse skin tumors (see, e.g., Shibata, *Stem Cells* 12:44–52 (1994)); (2) inhibition of animal carcinogenesis model systems (see, e.g., Kennedy, *Prev. Med.* 22:796–811 (1993); Johnson et al., *Cancer Chemother. Pharmacol.* 32:339–46 (1993)), such as nude mice or chimeric nude mice (see, e.g., Topp et al., *Blood* 82:2837–44 (1993); Sailkawa et al., *Jpn. J. Cancer Res.* 84:787–93 (1993)); (3) monocyte activation assay (Shi et al., *Cancer Res* 53:3986–91 (1993)); (4) serum tumor necrosis activity assay (Shi et al., *Cancer Res* 53:3986–91 (1993)); (5) croton oil induced ear edema in mice; and (6) croton oil induced ODC activity in mouse epidermis; the contents of which references are entirely incorporated herein by reference.

Additionally, predictive statistics and artificial intelligence can be used to provide computer programs which integrate matrix data to calculate patterns of activity, structural motifs, and a cell's expression of molecular targets to predict a given compound's mechanism of action to combine screening assay data and structure based drug design and testing. Weinstein et al., *Stem Cells* 12:12–22 (1994), the contents of which reference is entirely incorporated herein by reference.

Pharmaceutical Compositions. Pharmaceutical compositions comprising chalcone retinoid compounds of the present invention, include all compositions wherein at least one pharmaceutical compound or composition is contained in an amount effective to achieve its intended purpose. In addition, pharmaceutical compositions containing at least one pharmaceutical compound or composition may contain suitable pharmaceutically acceptable carriers comprising excipients and auxiliaries which facilitate processing of the active compounds into preparations which can be used pharmaceutically. Pharmaceutical compositions of the present invention can also include anti-neoplastics and/or immunomodulators.

A pharmaceutical compound or composition of the present invention may further comprise or consist essentially of at least one member selected from a single chain ribosome inhibitory protein (acting to block expression of a cancer related protein in a cancer related receptor cell or tissue); a cytokine; or a growth factor.

Cytokines that are produced by lymphocytes are termed lymphokines, whereas peptides produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells. Cytokines used according to the present invention are those suitable for use as additional active ingredients of compositions of the present invention.

According to another aspect of the present invention, a cytotoxic or a chemotherapeutic agent may be further included in a pharmaceutical composition of the present invention, optionally further comprising a delivery vector that preferentially binds to, or facilitates association of the pharmaceutical/diagnostic compound or composition with pathologic cells as target cells involved in cancer. The targets for this type of therapy can also be growth factor receptors, differentiation antigens, or other less characterized cell surface antigens specifically associated with cancer or precancer cells.

Pharmaceutical compositions can also include suitable solutions for administration by injection or orally, and contain from about 0.001 to 99 percent, preferably from about 20 to 75 percent of active component. Pharmaceutical compositions for oral administration include tablets and capsules. Compositions which can be administered rectally include suppositories.

Pharmaceutical carriers for the active ingredient may be either in sprayable or nonsprayable form. Non-sprayable forms can be semi-solid or solid forms comprising a carrier conducive to topical application and having a dynamic viscosity preferably greater than that of water. Also suitable for systemic or topical application, in particular to the mucous membranes and lungs, are sprayable aerosol preparations where the active ingredient is preferably in combination with a solid or liquid inert carrier material. The aerosol preparations can contain solvents, buffers, surfactants, perfumes, and/or antioxidants in addition to the retinoid compounds or compositions of the present invention.

Pharmaceutical Administration. Pharmaceutical administration of a pharmaceutical compound or composition of the present invention may be administered by any means that achieve its intended purpose, for example, to treat or prevent a cancer or precancerous condition.

The term "protection", as in "protection from a cancerous or precancerous condition", as used herein, encompasses "prevention," "suppression" or "treatment." "Prevention" involves administration of a pharmaceutical composition prior to the induction of the disease. "Suppression" involves administration of the composition prior to the clinical appearance of the disease. "Treatment" involves administration of the protective composition after the appearance of the disease. It will be understood that in human and veterinary medicine, it is not always possible to distinguish between "preventing" and "suppressing" since the ultimate inductive event or events may be unknown, latent, or not ascertained in the patient until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." See, e.g., Berkow et al, eds., *The Merck Manual*, 16th edition, Merck and Co., Rahway, N.J., 1992; Goodman et al., eds., *Goodman and Gilman's The Pharmacological Basis of Therapeutics*, 8th edition, Pergamon Press, Inc., Elmsford, N.Y., (1990); Katzung, *Basic and Clinical Pharmacology*, Appleton and Lange, Norwalk, Conn., (1992), which are entirely incorporated herein by reference, including all references cited therein. The "protection" provided need not be absolute, i.e., the disease need not be totally prevented or eradicated, provided that there is a statistically significant improvement (p=0.05) relative to a control population. Protection may be limited to mitigating the severity or rapidity of onset of symptoms of the disease.

At least one retinoid compound or composition of the present invention may be administered by any means that achieves the intended purpose, using a pharmaceutical composition as previously described.

For example, administration may be by various parenteral routes such as subcutaneous, intravenous, intradermal, intramuscular, intraperitoneal, intranasal, intracranial, transdermal, or buccal routes. Parenteral administration can also be by bolus injection or by gradual perfusion over time. Alternatively, or concurrently, administration may be by the oral route.

An additional mode of using of a pharmaceutical compound or composition of the present invention is by topical application. A pharmaceutical compound or composition of the present invention may be incorporated into topically applied vehicles such as salves or ointments.

A typical regimen for treatment or prophylaxis includes administration of an effective amount over a period of one or several days, up to and including between one week and about six months.

It is understood that the dosage of a pharmaceutical compound or composition of the present invention administered in vivo will be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage will be tailored to the individual subject, as is understood and determinable by one skilled in the relevant arts. See, e.g., Berkow et al, supra, Goodman et al, supra, and Katzung, supra; Avery's *Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references are entirely incorporated herein by reference.

The total dose required for each treatment may be administered by multiple doses or in a single dose. The pharmaceutical compound or composition may be administered alone or in conjunction with other pharmaceuticals directed to the pathology, or directed to other symptoms of the pathology.

Effective amounts of a pharmaceutical compound or composition of the present invention are from about 0.001 µg to about 100 mg/kg body weight, preferably about 5 mg/kg to 100 mg/kg body weight, most preferably about 20 mg/kg to 50 mg/kg body weight administered at intervals of 4–72 hours, for a period of 2 days to 5 years.

The compounds and/or compositions of the present invention are to be administered to preferably mammalian recipients, most preferably humans.

Having now generally described the invention, the same will be more readily understood through reference to the following example which is provided by way of illustration, and is not intended to be limiting of the present invention.

EXAMPLE 1

A Chalcone Retinoid Compound (I-N) According to Formula I

Preparation of 1-(3,5-di-t-butyl-4-methoxyphenyl)-3-[4-(4-acetaminophenoxycarbonyl)-phenyl]-2-propen-1-one having the formula $C_{33}H_{37}NO_5$, FW=527.67.

To a solution of 0.987 g (2.5 mmole) of 1-(3,5-di-t-butyl-4-methoxyphenyl)-3-(4-carboxyphenyl)-2-propen-1-one in 20 ml of anhydrous THF was added 0.251 g (2.75 mmole) of triethylamine. To this mixture was added dropwise, with stirring, 0.300 g (2.75 mmole) of ethyl chloroformate and stirred at room temperature for 1 h. Petroleum ether was added and the separated solid was filtered. The filtrate was concentrated in vacuo to dryness. The residue was taken by 20 ml of anhydrous acetonitrile and then 0.378 g (2.5 mmole) of acetaminophenol was added. The mixture was warmed and to this clear solution were with stirring added 0.25 g of triethylamine and 20 mg of 4-dimethylaminopyridine. The mixture was heated to 50° C. for 1 h. After removal of the solvent to a half volume the separating crystals were collected, washed,, and recrystallized from 95% ethanol, to obtain 0.995 g (75.4%) of the purified compound, having the characteristics of mp: 210°–212° C.; and MS (m/z) 527($M^+$), 377(100%), 349; Analysis for $C_{33}H_{37}NO_5$,FW=527.67 showed a calculated (%) of C:75.12, H:7.07, and N:2.56, with the actual (%) found to be C:75.46, H:7.05, and N:2.75.

EXAMPLE 2

A Chalcone Retinoid Compound (I-B) According to Formula I

Preparation of N-4-[4-(acetaminophenoxycarbonyl) phenyl]-3,5-di-t-butyl-4-hydroxybenzamide $C_{30}H_{34}N_2O_5$, FW=502.61.

Under the same conditions as described in Example 1, 0.80 g (32%) of the purified compound is obtained from the starting material of 1.85 g (5.0 mmole) of N-(4-carboxyphenyl)-3,5-di-t-butyl-4-hydroxy-benzamide. The characteristics of the purified compound are: mp: 332°–334° C. (ethanol) and MS (m/z) 502 ($M^+$), 369(100%), 352, 233.

EXAMPLE 3

A Chalcone Retinoid Compound (I-J) According to Formula I

Preparation of N-4-[4-(acetaminophenoxycarbonyl) phenyl]-3,5-di-t-butyl-4-methoxybenzamide $C_{31}H_{36}N_2O_5$, FW=516.64.

Under the same conditions as described in Example 1, 0.35 g (27.1%) of the purified compound is obtained from 0.960 g (2.5 mole) of N-(4-carboxyphenyl)-3,5-di-t-butyl-4-methoxybenzamide as the starting material. The characteristics of the purified compound are: mp: 248°–252° C. (85% ethanol), and MS (m/z)516 ($M^+$), 501, 411, 366 (100%), 247.

EXAMPLE 4

A Chalcone Retinoid Compound (I-Q) According to Formula I

Preparation of 4-[4-(acetaminophenoxycarbonyl)phenyl]-3,5-di-t-butyl-4-hydroxy-benzoate $C_{30}H_{33}NO_6$,FW=503.60.

Under the same conditions as described in Example 1, 0.25 g (20%) of the title compound is obtained from 0.926 g (2.5 mmole) of 4-carboxyphenyl 3,5-di-t-butyl-4-hydroxybenzoate as the starting compound. The characteristics of the title compound are: mp: 178°–190° C. (ethanol), MS (m/z) 503 ($M^+$), 353(100%), 233, 271.

EXAMPLE 5

A Chalcone Retinoid Compound (I-P) According to Formula I

Preparation of 1-(3,5-di-t-butyl-4-methoxy-phenyl)-3-[4-(4-carboxyphenylaminocarbonyl)phenyl]-2-propen-1-one $C_{32}H_{35}NO_5$,FW=513.64.

A mixture of 0.50 g (1.27 mmole) of 1-(3,5-di-t-butyl-4-methoxyphenyl)-3-(4-carboxyphenyl)-2-propen-1-one and 3 ml of thionyl chloride in 15 ml of benzene was heated under reflux for 15 min. After evaporation of the solvent the residue was dissolved in dry ether. The solution was added at room temperature with stirring to a mixture of 0.174 g (1.27 mmole) of 4-amino-benzoic acid and 2 ml of dry pyridine in anhydrous ether. The resulting mixture was stirred at room temperature for 4 h and set aside overnight. After removing the solvent, the residue was treated with water and acidified with dil. HCl to pH 3–4. The solid was collected and washed with water. The purified retinoyl compound-chalcone derivative was crystallized from dilute alcohol, with a yield of 0.4 g (51.3%), and the following characteristics: mp: 306°–308° C., and MS (m/z)513 ($M^+$), 498, 377(100%), 349, 319.

EXAMPLE 6

A Chalcone Retinoid Compound (I-A) According to Formula I

Preparation of N-4-[4-(hydroxyphenylaminocarbonyl) phenyl]-3,5-di-t-butyl-4-hydroxybenzamide $C_{28}H_{32}N_2O_4$, FW=460.58.

Under the same conditions as described in Example 1, 0.780 g (46.5%) of the purified compound, having a mp: 160°–162° C. (ethanol) is obtained from 1.347 g of N-(4-carboxyphenyl)-3,5-di-t-butyl-4-hydroxybenzamide as a starting material. Analysis showed a formula weight of $C_{28}H_{32}N_2O_4.H_2O$=469.59 with the calculated(%) as C: 71.73, H: 6.99, N: 5.56 and the found(%) as C: 71.95, H: 7.10, N: 5.84, with MS (m/z) 461 ($M^+$+1), 397(100%), 233.

EXAMPLE 7

A Chalcone Retinoid Compound (I-R) According to Formula I

Preparation of 4-(4-ethoxycarbonyl-phenylaminocarbonyl)phenyl 3,5-di-t-butyl-4-hydroxybenzoate $C_{31}H_{35}NO_6$,FW=517.63.

Under the same conditions as described in Example 1, 1.83 g (70.6%) of the purified compound is obtained from 1.85 g of 4-carboxyphenyl 3,5-di-t-butyl-4-hydroxybenzoate and 0.85 g of ethyl 4-aminobenzoate as the starting material. The characteristics of the purified compound are: mp: 162°–164° C. (ethanol) and MS (m/z) 517($M^+$), 502, 472, 284, 233(100%), 217, 164.

EXAMPLE 8

A Chalcone Retinoid Compound (I-S) According to Formula I

Preparation of 4-(4-carboxy-phenylaminocarbonyl) phenyl 3,5-di-t-butyl-4-hydroxybenzoate $C_{29}H_{31}NO_6$,FW= 489.57.

Excess aqueous 10% NaOH was added to a solution of the compound prepared in Example 7 in alcohol. The suspension was stirred at room temperature for 4 hrs and then set aside overnight. The resultant clear solution was neutralized by dilute HCl to pH 6 and evaporated. The residue was treated with water and acidified to pH 2–3 and 0.65 g (46%) of the purified solid was crystallized from dilute alcohol, having the following characteristics: mp>280° C. and MS (m/z) 489 ($M^+$), 474, 355, 257, 233(100%), 217, 121.

EXAMPLE 9

Synthesis of a Chalcone Retinoid Compound 4'-[(4-acetamino) phenoxycarbonylphenyl] 4-hydroxy-3,5-di-t-butyl-benzoate (I-Q)

To a solution of 2.5 mmol of p-carboxyphenyl 4-hydroxy-3,5-di-t-butyl-benzoate in 20 ml of anhydrous THF, 2.75 mmol of triethylamine was added at room temperature and stirred for 5 min. 2.75 mmol of ethyl chloroformate in 5 ml of THF was added dropwise to the mixture at room temperature and stirred for 2 hours. After 20 ml of petroleum ether was added, the mixture was filtered and the filtrate was evaporated in vaccuo to get a yellowish oil. The oil was dissolved in 20 ml of dry acetonitrile, and 2.5 mmol of acetaminophen was added with mild heating to get a clear solution. 2.75 mmol of triethylamine and a catalystic amount of 4-N,N-di-methyl-pyridine was then added and, then stirred at 50° C. for about 7 hr. The mixture was concentrated under reduced pressure, and neutralized with 10% HCl. The solid was crystallized with dilute ethanol. Yield: 20%; mp. 178°–9° C.; MS m/z: 503($M^+$, 3), 353(3), 233 (100), 121(50).

Microanalysis for $C_{30}H_{33}NO_6$=503.67

Calc. %: C 71.84, H 6.63. N 2.79 Fnd. %: 71.94, 6.50, 2.93

EXAMPLE 10

Synthesis of a Chalcone Retinoid Compound 4'-[(4-ethoxycarbonyl) phenylaminocarbonylphenyl] 4-hydroxy-3,5-di-t-butyl-benzoate (I-R)

Chalcone retinoid compound I-R was prepared as described in Example 9 but with ethyl p-amino-benzoate instead of acetaminophen. The title compound melt at 162°–4° C. Yield: 70.6%. MS m/z: 518(M+1, 4), 472(3), 233(100).

Microanalysis of $C_{31}H_{35}NO_6$=517.63

Calc. %: C 71.93, H 6.82, N 2.70 Fnd. %: 71.80, 6.80, 2.67

EXAMPLE 11

Synthesis of a Chalcone Retinoid Compound 4'-[(4-carboxy)phenylamino carbonylphenyl] 4-hydroxy-3,5-di-t-butyl-benzoate (I-S)

A mixture of 1.50 g of chalcone retinoid compound I-R in 10 ml of 95% ethanol and 5 ml of 10% NaOH was stirred at room temperature for a day and neutralized to pH 6, remove most of ethanol under reduced pressure, add 10 ml water and acidified to pH 1. The resulting white solid was crystallized with dilute ethanol. Yield: 46.0%; mp. >360° C.; MS m/z: 490(M+1, 55), 472(15), 258(60), 233(100).

EXAMPLE 12

Cell Differentiation Activity of Chalcone-Retinoids and Their Inhibitory Effect on Cancer Cells Human promyelocytic leukemia HL-60 cells were cultured in RPMI-1640 medium supplemented by 10% heat-inactivated calf serum and 100 U/ml of penicillin plus 100 µg/ml of streptomycin. The flasks containing cells and medium were incubated in an incubator with 5% $CO_2$ at 37° C. Log phase cells were seeded into the medium at a concentration of $1.2 \times 10^5$ to $1.4 \times 10^5$ cells per ml and cultured in flasks containing 5 ml of medium. Each group consisted of three flasks. Different concentrations of chalcone-retinoids were added. At intervals following the addition of chalcone-retinoids to the cultures, a small portion of cells was removed and live cells were counted under a light microscope using a dye-exclusion method with trypan blue. Cell differentiation was judged in terms of morphology and nitroblue tetrazolium (NBT) reduction.

For a determination of NBT reducing activity, a portion of the chalcone-retinoid-treated cells was removed at intervals following treatment and centrifuged. After centrifugation, 0.5 ml of 0.1% NBT (containing 100 ng TPA) was added to each tube. The contents of the test tubes were then incubated for 1 hour at 37° C. Cell smears were prepared from the cell sediment and stained using the Wright-Giemsa technique. For each smear prepared, 200 cells were isolated for examination under a light microscope with an oil immersion lens. Cells stained with blue-black granules were considered NBT-positive cells. The 50% differentiation or effective concentration ($ED_{50}$ or $EC_{50}$) is shown in terms of molar (M) concentration of the coumarin-retinoid tested.

For a determination of cell morphology, a cell smear was prepared at intervals following treatment of cells for each chalcone-retinoid concentration group using the Wright-Giemsa stain technique. Stained cells were counted and classified under a light microscope with an oil immersion lens. After treatment with chalcone-retinoids, the morphological development of HL-60 cells proceeded toward mature granulocytes. This development was manifested by decreased cell volume; a lower nuclei to cytoplasm ratio; smaller or missing nuclei; concentration of chromatin; and the appearance of a certain proportion of intermediate and late granuloblasts (progranulocytes), elongated rod granulocytes, and granulocytes with branched nuclei.

For a monolayer culture to test for the inhibitory effect of chalcone retinoids on cancer cells, 0.5 ml of trypsin solution (0.3 gm/ml) was added to the flasks for digestion. Microtiter plates (96 well) were used for the cell culture and 200 µl of cell suspension (1200 tumor cells) were placed in each well and incubated at 37° C. for 24 hours. Following the addition of the test compound, the control and treated flasks were placed in a $CO_2$ incubator for 5 day culture. For the MTT assay, 200 µl of MTT solution (5 mg in 10 ml of phosphate buffer) plus the medium were added and incubated for another 4 hours. Following incubation, the supernatant was discarded and 200 µl of DMSO was added to each well. With a mild agitation the OD values were determined by the MR 700 Elisa at 570 nm (reference wavelength was 450 nm). The $ED_{50}$ of the compound and tumor cell survival rate $$\text{Tumor cell survival} = \frac{OD \text{ of treated group}}{OD \text{ of control group}}$$

as percent inhibition were calculated.

TABLE 2

| Anti-neoplastic Activity of Chalcone-retinoid Compounds | | | |
|---|---|---|---|
| Compound | Retinoid | NBT $ED_{50}$ (mol/L) | MTT $ED_{50}$ (mol/L) |
| I-A | GR93107 | >$10^{-6}$ | $4.0 \times 10^{-6}$ |
| I-N | GR93108 | >$10^{-6}$ | $2.0 \times 10^{-6}$ |
| I-B | GR93109 | >$10^{-5}$ | $1.1 \times 10^{-5}$ |
| I-J | GR93110 | $1.2 \times 10^{-6}$ | $9.2 \times 10^{-7}$ |
| I-Q | GR93128 | $8.0 \times 10^{-6}$ | $6.0 \times 10^{-6}$ |
| I-R | GR93129 | >$10^{-5}$ | >$10^{-5}$ |
| I-S | GR93130 | >$10^{-5}$ | $1.6 \times 10^{-6}$ |

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A compound according to formula (I):

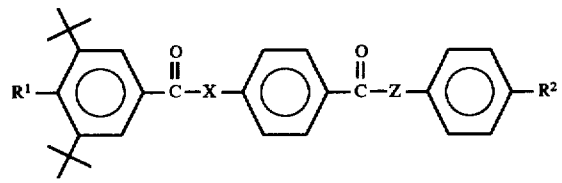

(I)

wherein $R^1$=OH or $C_1$-$C_5$ alkoxy; $R^2$=OH, carboxy, $C_1$-$C_5$ alkyl ester or NHCOR$^3$ where $R^3$=methyl, ethyl, propyl, or butyl; X=NH or $C_2$-$C_4$ alkenyl; and Z=NH or O.

2. A compound according to claim 1, wherein $R^1$=OH or CH$_3$O; $R^2$=OH, NHCOCH$_3$, NHCOC$_2$H$_5$, COOC$_2$H$_5$, COOH, COOCH$_3$, or COOC$_3$H$_7$; X=NH or CH=CH; and Z=NH or O.

3. A pharmaceutical composition comprising a compound according to claim 1 and a pharmaceutically acceptable carrier.

4. A pharmaceutical composition according to claim 3, further comprising at least one compound selected from an anti-cancer compound and an immunomodulator.

5. A compound according to claim 1, wherein said compound is selected from the group consisting of N-(3,5-Di-tert-butyl-4-hydroxybenzoyl)-p-aminobenzoic acid p-hydroxy-anilide, N-(3,5-Di-tert-butyl-4-hydroxybenzoyl)-p-aminobenzoic acid N-acetyl-p-aminophenol ester, N-(3,5-Di-tert-butyl-4-hydroxybenzoyl)-p-aminobenzoic acid p-ethoxycarbonyl-anilide, N-(3,5-Di-tert-butyl-4-hydroxybenzoyl)-p-aminobenzoic acid p-carboxy-anilide, 3',5'-Di-tert-butyl-4'-hydroxy-chalcone-4-carboxylic acid p-hydroxy-anilide, 3',5'-Di-tert-butyl-4'-hydroxy-chalcone-4-carboxylic acid N-acetyl-p-aminophenol ester, 3',5'-Di-tert-butyl-4'-hydroxy-chalcone-4-carboxylic acid p-ethoxycarbonyl-anilide, 3',5'-Di-tert-butyl-4'-hydroxy-chalcone-4-carboxylic acid p-carboxy-anilide, N-(3,5-Di-tert-butyl-4-methoxybenzoyl)-p-aminobenzoic acid p-hydroxy-anilide, N-(3,5-Di-tert-butyl-4-methoxybenzoyl)-p-aminobenzoic acid N-acetyl-p-aminophenol ester, N-(3,5-Di-tert-butyl-4-methoxybenzoyl)-p-aminobenzoic acid p-ethoxycarbonyl-anilide, N-(3,5-Di-tert-butyl-4-methoxybenzoyl)-p-aminobenzoic acid p-carboxy-anilide, 3',5'-Di-tert-butyl-4'-methoxy-chalcone-4-carboxylic acid p-hydroxy-anilide, 3',5'-Di-tert-butyl-4'-methoxy-chalcone-4-carboxylic acid N-acetyl-p-aminophenol ester, 3',5'-Di-tert-butyl-4'-methoxy-chalcone-4-carboxylic acid p-ethoxycarbonyl-anilide, 3',5'-Di-tert-butyl-4'-methoxy-chalcone-4-carboxylic acid p-carboxy-anilide, and isomers thereof.

* * * * *

UNITED STATES PATENT AND TRADEMARK OFFICE
CERTIFICATE OF CORRECTION

PATENT NO. : 5,703,130
DATED : Dec. 30, 1997
INVENTOR(S) : Han et al.

It is certified that error appears in the above-identified patent and that said Letters Patent is hereby corrected as shown below:

Column 1, line 25, delete "Hah et al., in vivo" and insert therefor --Han et al., In Vivo--;

Column 2, line 1, delete "retinic" and insert therefor --retinoic--;

Column 3, line 9, delete "in vivo" and insert therefor --In Vivo--;

Column 5, line 4, delete "anglogenesis" and insert therefor --angiogenesis--;

Column 8, line 5, delete "(p=0.05)" and insert therefor (p<0.05)--;

Column 9, line 15, delete "washed,," and insert therefor --washed,--.

UNITED STATES PATENT AND TRADEMARK OFFICE
CERTIFICATE OF CORRECTION

PATENT NO. : 5,703,130
DATED : December 30, 1997
INVENTOR(S) : Han, et. al.

It is certified that error appears in the above-identified patent and that said Letters Patent is hereby corrected as shown below:

Column 9, line 15, delete "washed,," and insert therefor --washed,--.

Signed and Sealed this

Seventh Day of April, 1998

Attest:

BRUCE LEHMAN

Attesting Officer

Commissioner of Patents and Trademarks